United States Patent [19]

Fráter et al.

[11] 4,120,974

[45] Oct. 17, 1978

[54] CERTAIN EPOXY COMPOUNDS IN ADMIXTURE AS INSECT REGULATING AGENTS

[75] Inventors: Georg Fráter, Greifensee; Albert Pfiffner, Bülach; Milos Suchy, Pfaffhausen; René Zürfluh, Bülach, all of Switzerland

[73] Assignee: Hoffmann-La Roche Inc., Nutley, N.J.

[21] Appl. No.: 755,362

[22] Filed: Dec. 27, 1976

[30] Foreign Application Priority Data

Jan. 9, 1976 [AT] Austria ................................. 105/76

[51] Int. Cl.² ...................... A01N 9/28; C07D 303/02
[52] U.S. Cl. ............................... 424/278; 260/348.57
[58] Field of Search .................. 424/278; 260/348 R, 260/348.57

[56] References Cited

U.S. PATENT DOCUMENTS

| | | | |
|---|---|---|---|
| 3,787,443 | 1/1974 | Erickson | 260/348 R |
| 3,879,429 | 4/1975 | Chodnekar et al. | 260/348 R |

Primary Examiner—V. D. Turner
Attorney, Agent, or Firm—Samuel L. Welt; Bernard S. Leon; George W. Johnston

[57] ABSTRACT

There is disclosed herein a novel compound, 6,7-epoxy-1-(p-ethylphenoxy)-3,4,7-trimethyl-nonane, which synergizes the insect regulation activity of 6,7-epoxy-1-(p-ethylphenoxy)-3-ethyl-7-methyl-nonane.

3 Claims, No Drawings

CERTAIN EPOXY COMPOUNDS IN ADMIXTURE AS INSECT REGULATING AGENTS

SUMMARY OF THE INVENTION

The present invention relates to the regulation of insect growth. More particularly, the invention is concerned with 6,7-epoxy-1-(p-ethylphenoxy)-3,4,7-trimethyl-nonane and insect growth regulation agents which contain said compound. This invention is also concerned with a method for the regulation of insect growth using said agents.

The phenyl derivative provided by the present invention is 6,7-epoxy-1-(p-ethylphenoxy)-3,4,7-trimethyl-nonane.

In accordance with the present invention it has been found that 6,7-epoxy-1-(p-ethylphenoxy)-3,4,7-trimethyl-nonane will synergize 6,7-epoxy-1-(p-ethylphenoxy)-3-ethyl-7-methyl-nonane in its action as a regulator of insect growth if 6,7-epoxy-1-(p-ethylphenoxy)-3-ethyl-7-methyl-nonane is present in an amount of at least 50% by weight in a mixture of these two active compounds. Another aspect of this invention is an insect growth regulation composition comprised of the foregoing compounds and an inert carrier material.

DESCRIPTION OF THE INVENTION

As used herein, the term "lower alkanol" connotes alkanols wherein the alkyl moiety is a straight or branched chain hydrocarbon having 1–6 carbon atoms. The term "halogen" connotes bromine, chlorine, fluorine and iodine. The term "alkali metal" connotes sodium, lithium and potassium. The term "alkaline earth metal" connotes calcium, magnesium and barium.

According to the process provided by this invention, 6,7-epoxy-1-(p-ethylphenoxy)-3,4,7-trimethyl-nonane (I) is prepared by (a) reacting a compound of the general formula

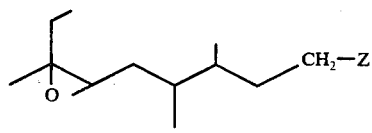

II wherein Z is halogen or a mesyloxy or tosyloxy group
with a phenolate of the general formula

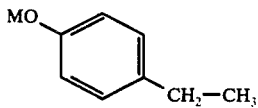

III wherein M represents an alkali metal or an alkaline earth metal or (b) hydrogenating 6,7-epoxy-1-(p-ethylphenoxy)-3,4,7-trimethyl-2-nonene, or (c) epoxidizing p-ethylphenyl 3,4,7-trimethyl-6-nonenyl ether.

The reaction of a compound of formula II with a phenolate of formula III in accordance with embodiment (a) of the present process is carried out in inert organic solvents such as ethers, amides or acetals. Particularly preferred solvents are dimethylformamide, dioxan, hexamethylphosphoric acid triamide, tetrahydrofuran or dimethoxyethane or in a combination of two or more of these solvents. The reaction is conveniently carried out using the phenol corresponding to the phenolate of formula III and in the presence of an alkali metal or alkaline earth metal, its corresponding hydride or amide or an alkali metal hydroxide. By this means, the corresponding phenolate is formed from the phenol. Preferred alkali metals are sodium and potassium and preferred alkaline earth metals are calcium and magnesium. The temperature at which the reaction is carried out is of no particular significance, but the temperature will generally vary between −20° C. and the boiling point of the reaction mixture. Preferably, the reaction is carried out at room temperature, particularly when Z in formula II is bromine.

The hydrogenation of 6,7-epoxy-1-(p-ethylphenoxy)-3,4,7-trimethyl-2-nonene in accordance with embodiment (b) of the present process is expediently carried out using catalytically activated hydrogen in an inert organic solvent such as lower alkanols or esters thereof, particularly ethyl acetate or methanol. The hydrogenation is usually carried out at a temperature between room temperature and the boiling point of the solvent and at normal or elevated pressure. Suitable catalysts are, for example, Raney nickel, noble metals and noble metal oxides such as platinum, palladium or the oxides thereof.

The epoxidation of p-ethylphenyl 3,4,7-trimethyl-6-nonenyl ether in accordance with embodiment (c) of the present process is expediently carried out by dissolving said ether in a halogenated hydrocarbon such as methylene chloride or chloroform, and treating the solution obtained with an organic peracid such as perbenzoic acid, m-chloroperbenzoic acid or perphthalic acid at a temperature between 0° C. and room temperature. Alternatively, said ether may be suspended in water, treated with a sufficient amount of an inert solvent such as dioxane, tetrahydrofuran or 1,2-dimethoxyethane to provide a homogeneous, concentrated solution and followed by the introduction of N-bromosuccinimide portionwise into this solution at a temperature between 0° C. and room temperature. The bromohydrin can be converted smoothly into the desired epoxide by the action of alkalis, especially sodium methylate in methanol.

6,7-Epoxy-1-(p-ethylphenoxy)-3,4,7-trimethyl-nonane synergizes the insect growth regulator properties of 6,7-epoxy-1-(p-ethylphenoxy)-3-ethyl-7-methyl-nonane. This synergistic effect manifests itself when the relative proportions of these two compounds, in percent by weight, are such that 6,7-epoxy-1-(p-ethylphenoxy)-3-ethyl-7-methyl-nonane is present in an amount of 50% or more. A suitable ratio is 50% to 90% of 6,7-epoxy-1-(p-ethylphenoxy)-3-ethyl-7-methyl-nonane and 50% to 10% of 6,7-epoxy-1-(p-ethylphenoxy)-3,4,7-trimethyl-nonane. A ratio of 60% to 85% to 40% to 15% is preferred, with 70% to 80% to 30% to 20% being particularly preferred and 75% to 25% being especially preferred (i.e., a mixture in the ratio 3:1).

In contrast to most of the hitherto known pesticides, which kill, paralyze or drive away the pests as contact- and feed poisons, the pesticide according to the invention interferes with the hormonal system of the pest organism. In insects, for example, the metamorphosis to the imago, the laying of viable eggs and the development of laid normal eggs are disturbed. The sequence of generations is interrupted and the insects are indirectly killed. The pesticide is practically non-poisonous to vertebrates, the toxicity lying at about 1000 mg/kg body weight. The present pesticide is also easily degraded, thus excluding the danger of an accumulation. The pesticide can accordingly be used without hesitation for combatting pests in animals, plants and provisions.

The pesticide according to the present invention is suitable for combatting invertebrate pests, particularly Arthropoda and Nematoda and especially insects of the order Diptera, Lepidoptera, Homoptera, Hymenoptera, Coleoptera, Orthoptera, Heteroptera, Psocoptera, Thysanoptera, Neuroptera and Blattida, of Arachnida of the order Acarina and of Nematoda of the order Tylenchoidea such, for example, Aedes aegypti (yellow fever mosquito), Ceratitis capitata (mediterranean fruit fly), Culex pipiens (common midge), Aedes taeniorhynchus, Anopheles stephensi, Calliphora sp., Musca domestica (house fly), Adoxophyes reticulana (fruit-peel moth), Ephestia kuhniella (mealmoth), Galleria mellonella (wax moth, large), Heliothis virescens, Laspeyresia pomonella (codlin moth, fruit worm), Ostrinia nubilalis (corn borer), Plodia interpunctella (dried-fruit moth), Plutella xylostella (cabbage moth), Tineola biselliella (clothes moth), Aphis fabae (bean aphid, black), Aphis pomi (green apple aphid), Aonidiella aurantii (Californian orange scale louse), Aspidiotus hederae (Oleander scale louse), Coccus hesperidum (Lecania scale louse), Myzus persicae (green peach aphid), Planococcus citri (greenhouse louse), Megoura viciae, Trialeurodes vaporarium (white greenhouse fly), Encarsia formosa, Habrobracon juglandis, Syrphus corollae, Dermestes maculatus (spined bacon beetle), Epilachna chrysomelina (cucumber beetle, speckled), Leptinotarsa decemlineata (Colorado beetle), Oryzaephilus surinamensis (cereal beetle), Otiorrhynchus sulcatus (widemouthed weevil, sulcate), Rhizopertha dominica (cereal capsid), Sitophilus granarius R + S (common grain weevil), Stiophilus oryzae R + S (rice weevil), Tenebrio molitor (common meal weevil), Tribolium castaneum R + S (rice-flour beetle, red-brown), Trogoderma granarium (Khapra beetle), Blatella germanica (cockroach), Leucophaea surinamensis, Nauphoeta cinerea (gravel cockroach), Blatta orientalis, Periplaneta americana, Dysdercus cingulatus (cotton bug, cotton stainer), Rhodnius prolixus (shrub bug), Tetranychus urticae (bean spider mite), Tetranychus cinnabarinus (carmine spider mite), Phytoseilus macropilis (preying mite), Panonynchusulmi, Ditylenchus dipsaci (stalk nematode), Heterodera cruciferae (cabbage cyst nematode), Meloidogyne sp. (root gall nematode) [R = resistant strain; S = sensitive strain].

The pesticide according to the invention can be used in the form of concentrates, granules or, together with carriers, in the form of sprays, aerosols or powders. For certain purposes, it may be advantageous to use emulsions, suspensions or solutions which contain emulsifiers or wetting agents. As carriers there may be mentioned, for example, chalk, talc, bentonite, keolin, diatomaceous earth, siliceous earth, Fuller's earth, lime, gypsum, powders and dusts from organic waste products, polymers such as polyvinyl chloride, polyethylene, polyacrylate, polystyrene and mixed polymerizates, etc. The corresponding formulations can also contain additives such as, for example, antioxidants, ultraviolet-absorbers and other stabilizers as well as odorants and baits, etc. It is also possible to provide formulations which liberate the active substance mixture in dosed amounts; for example, microcapsules, coated granules, solutions in polymeric substances, etc. It will be appreciated that the foregoing are given by way of example and are in no way intended to limit the invention.

In general, the pesticide of the present invention can be formulated according to the procedures described, for example, in Farm Chemicals, Volume 128, page 52, et seq. The pesticide can also contain other additives such as emulsifiers or masking agents.

The pesticide according to the invention can be made up in the form of concentrates which are suitable for storage and transport. Such concentrates can contain, for example, 40–90% of the synergistically active combination of the two active compounds aforesaid. These concentrates can be diluted with the same or a different carrier material to provide concentrations which are suitable for practical use. In a ready-for-use agent concentrations of active compounds of, for example, 0.1–20, preferably 0.1–10, percent by weight can be present. The concentration of active compounds can, however, also be smaller or larger.

As will be evident from the following Examples, an amount of $10^{-4}$–$10^{-6}$ g/cm$^2$, i.e., a spray mixture concentration of 10%–0.1% (active compound mixture in the ratio 3:1), is sufficient to achieve the desired effect.

The pesticide according to the invention can be used against pests according to customary methods such as, for example, by contact or by intake with the food.

The following non-limiting Examples are illustrative of the present invention.

6,7-Epoxy-1-(p-ethylphenoxy)-3,4,7-trimethyl-2-nonene is preferably prepared from 2-methyl-acetoacetic ester which, in turn, is normally prepared as follows.

EXAMPLE 1

3,6-Dimethyl-oct-5-en-2-one 144.4 g. of ethyl 2-methyl-acetoacetate are added dropwise to a solution of 61 g. of sodium ethylate in 1.3 liters of ethanol while cooling with ice. After ca. 15 minutes, the resulting sodium enolate is treated dropwise at 0°–5° C. with 130 g. of 3-methyl-pent-2-ene-1-bromide. After 3 hours at room temperature, the alkylation has finished and the mixture is treated with 1.1 liters of 2-N sodium hydroxide solution. The resulting mixture is then heated under reflux for 2 hours. The mixture is then poured onto ice-water and extracted with ether. The ether phase is dried over sodium sulfate and evaporated, the residue being purified by distillation. There is obtained pure 3,6-dimethyl-oct-5-en-2-one of boiling point 72°–74° C./12 mmHg.

EXAMPLE 2

Ethyl 3,4,7-trimethyl-2,6-nonadienecarboxylate 260 g. of ethyl (O,O-diethyl-phosphono)acetate dissolved in 700 ml. of dimethoxyethane, are added dropwise to 55.6 g. of sodium hydride suspended in 300 ml. of dimethoxyethane. After cessation of the evolution of hydrogen, a solution of 75 g. of 3,6-dimethyl-oct-5-en-2-one in 300 ml. of dimethoxyethane is added dropwise to the "ylid solution" and the mixture is stirred for 18 hours at 40° C. The mixture is poured onto ice-water and extracted with ether. The ether phase is dried over sodium sulfate and evaporated, the residue being purified by distillation. There is obtained ethyl 3,4,7-trimethyl-2,6-nonadienecarboxylate of boiling point 75°–81° C./0.07 mmHg.

EXAMPLE 3

3,4,7-Trimethyl-2,6-nonadien-1-ol 157 g. of ethyl 3,4,7-trimethyl-2,6-nonadienecarboxylate are dissolved in 300 ml. of benzene and added dropwise while cooling with ice to a solution of 370 g. of 70% sodium bis-(methoxyethoxy)-aluminum hydride in benzene. The mixture is then stirred at 40° C. for 2 hours and subsequently worked up with water/ether as described earlier. The 3,4,7-trimethyl-2,6-nonadien-1-ol obtained boils at 79°–84° C./0.09 mmHg.

EXAMPLE 4

3,4,7-Trimethyl-2,6-nonadiene-1-bromide 26 g. of 3,4,7-trimethyl-2,6-nonadien-1-ol and 1 ml. of pyridine are introduced into 200 ml. of pentane and the mixture is treated at −5° C. while stirring with 15 g. of phosphorus tribromide. After completion of the addition, the mixture is stirred for a further 2 hours at 0° C., then poured onto ice-water and extracted with pentane. The pentane phase is shaken with saturated potassium hydrogen carbonate solution and sodium chloride solution, dried over sodium sulfate and evaporated. The 3,4,7-trimethyl-2,6-nonadiene-1-bromide, which is uniform on thin-layer chromatography plates, is used without further purification.

EXAMPLE 5 p-Ethylphenyl 3,4,7-trimethyl-2,6-nonadienyl ether 89 g. of p-ethylphenol are dissolved in 610 ml. of N,N-dimethylformamide and treated with a solution of 42 g. of potassium hydroxide solution in 66 ml. of water. 120 g. of crude 3,4,7-trimethyl-2,6-nonadiene-1-bromide are then added dropwise at 20° C. The mixture is stirred for 16 hours, poured onto water and extracted with ether. The ether phase is extracted three times with 10% potassium hydroxide solution, washed with water until neutral, dried over sodium sulfate and evaporated. After chromatography on silica gel with hexane/ethyl acetate (7:3) as the eluting agent, there is obtained pure p-ethylphenyl 3,4,7-trimethyl-2,6-nonadienyl ether of boiling point 130°–135° C./0.01 mm.

EXAMPLE 6

6,7-Epoxy-1-(p-ethylphenoxy)-3,4,7-trimethyl-2-nonene 10 g. of p-ethylphenyl 3,4,7-trimethyl-2,6-nonadienyl ether are dissolved in 110 ml. of dichloromethane and treated portionwise at −10° C. with 7.8 g. of 80% m-chloroperbenzoic acid. After completion of the treatment, the mixture is stirred for a further 2 hours at 0° C., shaken out with 10% sodium sulfite solution, 1-N sodium hydroxide solution and water, dried over sodium sulfate and evaporated. There is obtained pure 6,7-epoxy-1-(p-ethylphenoxy)-3,4,7-trimethyl-2-nonene; NMR (CDCl$_3$): 7.25–6.7 ppm (AB-quartet of the four aromatic protons); 5.5 ppm (a vinyl proton at C-2); 4.52 ppm doublet of the —O—CH$_2$ group); 2.59 ppm (quartet of the aromatic-bound —CH$_2$ group); 2.8–2.2 ppm (multiplet of the protons at C-4 and C-6); 1.65 ppm (wide singlet of the methyl group at C-3); 1.78–0.8 ppm (complicated multiplet of 19 protons).

EXAMPLE 7

19.8 g. of 6,7-epoxy-1-(p-ethylphenoxy)-3,4,7-trimethyl-2-nonene are hydrogenated in 500 ml. of ethyl acetate in the presence of 800 mg. of platinum (IV) oxide (PtO$_2$). After the uptake of 1 mol of hydrogen, the catalyst is filtered off and the filtrate evaporated. Liquid impurities formed during the hydrogenation are distilled off at 100° C./12 mmHg. The residual light-colored oil is pure 6,7-epoxy-1-(p-ethylphenoxy)-3,4,7-trimethyl-nonane; NMR (CDCl$_3$); 7.25–6.7 ppm (AB quartet of the four aromatic protons), 4.0 ppm (triplet of the —O—CH$_2$ group), 2.6 ppm (quartet of the aromatic-bound —CH$_2$ group), 2.77 ppm (triplet of the protons on the epoxide ring), 2.01–0.75 ppm (complicated multiplet of 23 protons).

EXAMPLE 8

The mixture of active compounds for the biological experiments is formulated as follows:

|  | g/l |
|---|---|
| 6,7-epoxy-1-(p-ethylphenoxy)-3-ethyl-7-methyl-nonane | 375.0 |
| 6,7-epoxy-1-(p-ethylphenoxy)-3,4,7-trimethyl-nonane | 125.0 |
| Tensiofix FAB (mixture of castor oil and ethylene oxide condensation products with ca 25 mols of ethylene oxide in the ratio 3:1) | 100.0 |
| Edenol D 81 (ethoxylated soya oil with an oxirane oxygen content of 6%) | 25.0 |
| BHT (butylated hydroxytoluene) | 10.0 |
| Shellsol Ab (mixture of mono-, di- and tri-lower alkylbenzenes) | to 1000 ml |

EXAMPLE 9

The active compound 6,7-epoxy-1-(p-ethylphenoxy)-3-ethyl-7-methyl-nonane is formulated for the biological experiments as follows:

|  | g/l |
|---|---|
| 6,7-epoxy-1-(p-ethylphenoxy)-3-ethyl-7-methyl-nonane | 500.0 |
| Tensiofix FAB (mixture of castor oil and ethylene oxide condensation products with ca 25 mols of ethylene oxide in the ratio 3:1) | 100.0 |
| Edenol D 81 (ethoxylated soya oil with an oxirane oxygen content of 6%) | 25.0 |
| BHT (butylated hydroxytoluene) | 10.0 |
| Shellsol AB (mixture of mono-, di- and tri-lower alkylbenzenes) | to 1000 ml |

EXAMPLE 10

The active compound 6,7-epoxy-1-(p-ethylphenoxy)-3,4,7-trimethyl-nonane is formulated for the biological experiments as follows:

|  | g/l |
|---|---|
| 6,7-epoxy-1-(p-ethylphenoxy)-3,4,7-trimethyl-nonane | 500.0 |
| Tensiofix FAB (mixture of castor oil and ethylene oxide condensation products with ca 25 mols of ethylene oxide in the ratio 3:1 | 100.0 |
| Edenol D 81 (ethoxylated soya oil with an oxirane oxygen content of 6%) | 25.0 |
| BHT (butylated hydroxytoluene) | 10.0 |
| Shellsol AB (mixture of mono-, di- and tri- lower alkylbenzenes) | to 1000 ml |

EXAMPLE 11

*Culex pipi

Small glasses are filled with 100 ml. of tap water and then a solution containing the active compound(s) to be tested in the desired concentration is added. The glasses are then sealed with a plastic sheet and incubated in an Ecophyten at 28° C. and 85% relative humidity for 6 days while irradiating with ultraviolet light. After this incubation, 20 *Culex pipiens pipiens* larvae in the fourth larval stage are placed in each glass and kept under optimum conditions (28° C., 85% relative humidity, 14 hours light) until the development to the adult has ended. The action of the insect growth regulator (IGR) is indicated in the percentage reduction of adult insects in comparison with untreated larvae (comparison experiment without active compound). In the comparison experiment the mortality was 5%.

Table 1

| Dosage $10^{-x}$ g/cm$^2$ | X | % Activity |
|---|---|---|
| Formulation according to Example 8 | 7 | 59 |
| Formulation according to Example 9 | 7 | 21 |
| Formulation according to Example 10 | 7 | 0 |

EXAMPLE 12

*Culex pipiens pipiens* - Test

Method

Small glasses are filled with 100 ml. of tap water and two dessertspoonful of earth and a solution containing the active compound(s) to be tested in the desired concentration is subsequently added. The glasses are then sealed with a plastic sheet and incubated in an Ecophyten at 28° C. and 85% relative humidity for 6 days. After this incubation, 20 *Culex pipiens pipiens* larvae in the fourth larval stage are placed in each glass and kept under optimum conditions (28° C., 85% relative humidity, 14 hours light) until the development to the adult has ended. The action of the insect growth regulator (IGR) is indicated in the percentage reduction of adult insects in comparison with untreated larvae (comparison experiment without active compound). In the comparison experiment the mortality was 6%.

Table II

| Dosage $10^{-x}$ g/cm$^2$ | X | % Activity |
|---|---|---|
| Formulation according to Example 8 | 7 | 91 |
| Formulation according to Example 9 | 7 | 56 |
| Formulation according to Example 10 | 7 | 0 |

EXAMPLE 13

*Aphis fabae* - Test

Method

Field bean plants are sprayed with a solution containing the active compound(s) to be tested in the desired concentration until a complete spray layer is obtained. After drying the spray layer, the plants are incubated for 7 days at 30° C. while irradiating with ultraviolet light. The plants are then each infested with 10 moving female animals. After 2 days, the P generation (adult animals) is removed.

Evaluation

The evaluation is carried out after the appearance of the F$_2$ generation (second generation of young animals) in the untreated control experiment. As soon as the F$_2$ generation appears in the control experiment, the number of the F$_1$ and F$_2$ bean aphids in the experiment is determined (first and second generation of young animals). The result is indicated in the percentage reduction of the total population in comparison with the control.

Table III

| Dosage $10^{-x}$ g/cm$^2$ | X | % Activity |
|---|---|---|
| Formulation according to Example 8 | 6 | 82 |
| Formulation according to Example 9 | 6 | 66 |
| Formulation according to Example 10 | 6 | 0 |

EXAMPLE 14

*Myzus persicae* - Test

Method

Chinese mustard plants are sprayed with a solution containing the active compound(s) to be tested in the desired concentration until a complete spray layer is obtained. After drying the spray layer, the plants are infested with 10 moving female animals and incubated at 25° C.

Evaluation

The evaluation is carried out after the appearance of the F$_2$ generation (second generation of young animals) in the untreated control experiment. As soon as the F$_2$ generation appears in the control experiment the number of the F$_1$ and F$_2$ bean aphids in the experiment is determined (first and second generation of young animals). The result is indicated in the percentage reduction of the total population in comparison with the control.

Table IV

| Dosage $10^{-x}$ g/cm$^2$ | X | % Activity |
|---|---|---|
| Formulation according to Example 8 | 7 | 82 |
| Formulation according to Example 9 | 7 | 0 |
| Formulation according to Example 10 | 7 | 0 |

EXAMPLE 15

*Epilachna chrysomelina* - Test

Method

Two-leaved pumpkin plants in pots are sprayed with a solution containing the active compound(s) to be tested in the desired concentration until a complete spray layer is obtained. After drying the spray layer, the plants are incubated for 7 days at 30° C. while irradiating with ultraviolet light. The plants are then each infested with 5 animals in the fourth larval stage.

Evaluation

After the adult animals have hatched in the untreated controls, the number of adult animals on the treated plants are determined. The result is indicated in the percentage reduction of normal adult animals in comparison with the controls. In the comparison experiment the mortality was 10%.

Table V

| Dosage $10^{-x}$ g/cm$^2$ | X | % Activity |
|---|---|---|
| Formulation according to Example 8 | 6 | 50 |
| Formulation according to Example 9 | 6 | 0 |
| Formulation according to Example 10 | 6 | 0 |

EXAMPLE 16

*Adoxophyes orana* - Test

Method

Petri dishes are treated with an acetone solution of the test mixture or the test compound. The test mixture (C) comprises a 1:1 mixture of 6,7-epoxy-1-(p-ethylphenoxy)-3-ethyl-7-methyl-nonane (A) and 6,7-epoxy-1-(p-ethylphenoxy)-3,4,7-trimethyl-nonane (B) and the test compounds comprise the individual compounds denoted as (A) and (B). Half of all treated petri dishes are exposed to ultraviolet light (Philips TLA 40W/05) for 6 days and the remainder are exposed to ultraviolet light from the same source for 14 days. Thereafter, 10 *Adoxophyes orana* larvae in the last larval stage are placed in each petri dish, fed with synthetic feed and kept at 25° C. and 60% room humidity. Untreated petri dishes serve as controls. The duration of the test is 21–30 days.

Evaluation

After the adult animals in the untreated controls have hatched, the result is expressed in the percentage of normal adult animals in comparison with the controls. In the experiment which is reported in Table VI hereinafter the mortality of the controls amounts to 4% and in the experiment which is reported in Table VII hereinafter the mortality of the controls is 2%.

Table VI

| Results after 6 days ultraviolet exposure | | |
|---|---|---|
| Dosage $10^{-X}$ g/cm$^2$ | X | % Activity |
| A | 6 | 20 |
| B | 6 | 20 |
| C | 6 | 75 |

Table VII

| Results after 14 days ultraviolet exposure | | |
|---|---|---|
| Dosage $10^{-X}$ g/cm$^2$ | X | % Activity |
| A | 5 | 18 |
| B | 5 | 18 |
| C | 5 | 54 |

EXAMPLE 17

*Epilachna chrysomelina* - Test

Method

Two-leaved pumpkin plants in pots are sprayed with an acetone solution of the mixture (C) and of the individual components (A) and (B) until a complete spray layer is obtained. The mixture (C) comprises 6,7-epoxy-1-(p-ethylphenoxy)-3-ethyl-7-methylnonane (A) and 6,7-epoxy-1-(p-ethylphenoxy)-3,4,7-trimethyl-nonane (B) in the ratio 1:1. The individual components (A) and (B) of this mixture (in acetone solution) are also tested. After drying the spray layers, the plants are infected with five larvae in the last larval stage and incubated at 26° C. and 60% room humidity, the plants being covered with Cellophane film. Untreated plants serve as controls. The duration of the test is 17–20 days.

Evaluation

After the adult animals in the untreated controls have hatched, the adult animals on the treated plants are determined. The result is expressed in the percentage reduction of normal adult animals in comparison with the controls. In the experiment reported in Table VIII hereinafter the mortality in the controls amounts to 7% and in the experiment reported in Table IX hereinafter the mortality in the controls amounted to 15%.

Table VIII

| Dosage $10^{-X}$ g/cm$^2$ | X | % Activity |
|---|---|---|
| A | 6 | 4 |
| B | 6 | 0 |
| C | 6 | 36 |

Table IX

| Dosage $10^{-X}$ g/cm$^2$ | X | % Activity |
|---|---|---|
| A | 5 | 76 |
| B | 5 | 6 |
| C | 5 | 100 |

We claim:

1. A composition for the regulation of insect growth, said composition containing as active compounds about 50% to about 75% by weight 6,7-epoxy-1-(p-ethylphenoxy)-3-ethyl-7-methyl-nonane and about 50% to about 25% by weight 6,7-epoxy-1-(p-ethylphenoxy)-3,4,7-trimethylnonane relative to the total weight of these two active compounds.

2. A composition according to claim 1 which contains 75% by weight of 6,7-epoxy-1-(p-ethylphenoxy)-3-ethyl-7-methyl-nonane and 25% by weight of 6,7-epoxy-1-(p-ethylphenoxy)-3,4,7-trimethyl-nonane relative to the total weight of these two active compounds.

3. A method for the regulation of insect growth which comprises contacting said insects with a composition comprising as active compounds about 50% to about 75% by weight 6,7-epoxy-1-(p-ethylphenoxy)-3-ethyl-7-methyl-nonane and about 50% to about 25% by weight 6,7-epoxy-1-(p-ethylphenoxy)-3,4,7-trimethyl-nonane relative to the total weight of these two active compounds.